(12) United States Patent
Eden

(10) Patent No.: US 6,605,446 B2
(45) Date of Patent: Aug. 12, 2003

(54) DETECTING AIRBORNE MICROORGANISMS

(76) Inventor: Gideon Eden, 2765 Ember Way, Ann Arbor, MI (US) 48104

( * ) Notice: Subject to any disclaimer, the term of this patent is extended or adjusted under 35 U.S.C. 154(b) by 0 days.

(21) Appl. No.: 09/992,561

(22) Filed: Nov. 16, 2001

(65) Prior Publication Data

US 2003/0077690 A1 Apr. 24, 2003

Related U.S. Application Data

(60) Provisional application No. 60/343,578, filed on Oct. 18, 2001.

(51) Int. Cl.[7] ................................. C12Q 1/04
(52) U.S. Cl. .................... 435/34; 435/283.1; 435/287.1
(58) Field of Search ........................ 435/283.1, 287.1, 435/34

(56) References Cited

U.S. PATENT DOCUMENTS 5,766,958 A * 6/1998 Sullivan et al. ............. 436/174

2002/0062702 A1 * 5/2002 Bradley .................... 73/864.34

OTHER PUBLICATIONS

Davies, Methods in Microbiology vol. 4 XIV, pp. 367–404, edited by Booth, Academic Press (1971).*

Husmann et al., "Detection of Airborne Viable Germs in Cleanrooms with a Fluoresecene Marking Method", Pharm. Ind. 62 (10): 805–811 (2000).*

* cited by examiner

*Primary Examiner*—Sandra E. Saucier
(74) *Attorney, Agent, or Firm*—James M. Deimen

(57) ABSTRACT

A new apparatus and method for collecting and detecting airborne microorganisms comprises a culturing container containing liquid media capable of growing the suspect microorganisms and a pump for drawing an air sample containing the suspect microorganisms through the liquid media. The suspect microorganisms mix with the liquid media and are subsequently incubated to promote their growth and cause an indication of their presence.

21 Claims, 1 Drawing Sheet

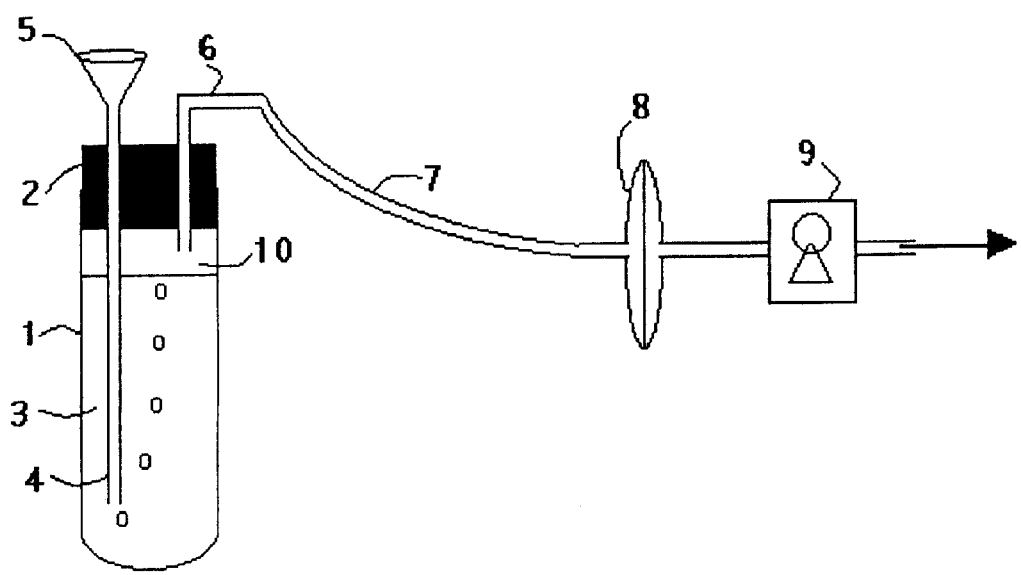
Figure

US 6,605,446 B2

DETECTING AIRBORNE MICROORGANISMS

CROSS REFERENCES TO RELATED APPLICATIONS

This application claims the benefit of Provisional Patent Application Ser. No. 60/343,578 filed Oct. 18, 2001.

BACKGROUND—Field of Invention

This invention relates to a device and method for detecting the presence and measuring the amount and activity of airborne bacterial contamination.

BACKGROUND—Description of Prior Art

There is always a concern about airborne contaminants, especially pathogenic bacteria. Consequently, there is a constant need for ambient air monitoring in conjunction with manufacturing and packaging of food, pharmaceutical products, hospital environments and other industrial and clinical facilities. Lately, with the introduction and spread of biological warfare this ambient monitoring issue is becoming critical in a variety of situations.

Prior testing devices perform qualitative and quantitative analyses of ambient air contamination by microorganisms. All of the known devices in the prior art employ an impeller to draw in contaminated air and to cause the micrrganisms to be impacted against solidified culture medium. The most successful types of samplers have been the slit-to-agar (STA) devices that utilize a revolving agar plate under a split-type orifice, to impinge the air sample directly upon a nutrient-collecting medium of solidified agar. Viable microorganisms immediately find nutrients suitable for their growth in the collection medium. Such devices are disclosed in U.S. Pat. Nos. 5,500,369 and 5,831,182. However, the test results of these air samplers have been inconsistent. This is due to the basic assumption of the tests that the collected bacteria are equally distributed in the tested atmosphere. However, testing a small portion of air in a large room may result in false negative determinations. Unfortunately these devices cannot sample large portions of air since the agar surfaces can easily dry by the long exposure to the air stream and consequently turn ineffective in growing the microorganisms.

Furthermore, prior art samplers are very difficult to completely sanitize. Cross contamination of samples can easily occur, and accumulation of particulate matter can jeopardize the critical measurements. Sanitation of the prior art samplers and their components is very time consuming and labor intensive and as such a great demand on the operators. Only professionals can actually ensure reliable operation and interpretation of results generated by these devices.

SUMMARY OF THE INVENTION

The new apparatus and method for collecting and detecting airborne microorganisms comprises a culturing container containing liquid media capable of growing the suspect microorganisms and a pump for drawing an air sample containing the suspect microorganisms through the liquid media. The suspect microorganisms mix with the liquid media and are subsequently incubated to promote their growth and cause an indication of their presence.

OBJECTS AND ADVANTAGES

Accordingly, among the several objects and advantages of my invention are to provide a small and portable device that can sample any amount of air in an accumulative manner. The device can be operated with a small rechargeable battery and can be applied in tight places. Most of its components are disposable in order to minimize or completely eliminate sterilization processes. Consequently, the device is easy to operate and does not require highly trained professional personnel for its normal operation. The shelf life of the chemical ingredients are considerably increased because evaporation is not significant during storage. Due to its size and the simplicity of its operation the disclosed device can be used in remote areas where warfare contamination is expected.

Still further objects and advantages will become apparent from a consideration of the ensuing description and accompanying drawings.

BRIEF DESCRIPTION OF THE DRAWING

The FIGURE shows a block diagram of an air-sampling device according to the preferred embodiment of the invention.

PREFERRED EMBODIMENT—Description

As illustrated in FIG. 1, the disclosed sampler includes a culturing container 1 in which liquid nutrient media 3 is contained. Specially formulated media, selective or non-selective can be utilized. Under the appropriate incubation temperature a selected class of microorganisms can optimally grow. The media can also include indicator substances to detect chemical changes occurring in the media due to metabolic processes associated with microbial growth. Dye or fluorescence indicators sensitive to pH, redox or enzymatic reactions can be utilized for selective and non-selective detection of microbial growth. The magnitude of the bio-burden i.e. bacterial concentration can also be measured, as explained below.

The container 1 is sealed with a cap 2 such that headspace 10 is kept above the liquid media 3. A collection tube 4 is embedded in the cap 2 and extended below the cap and immersed in the liquid reaching the bottom section of the container. The upper part 5 of the tube 4 is opened to the ambient where the air sample is drawn. A suction tube 6 is also embedded in the cap 2 extending downwards to the headspace 10 of the container. The suction tube 6 is linked via a flexible tube 7 to an in-line air filter 8 connected to a vacuum pump 9. The purpose of the filter is to prevent any contaminant from reaching the vacuum pump 9 and disturbing its operation. Therefore, the pore size of the filter should be in the sub-micron range.

One of the obvious advantages of this configuration is that most components are disposable. The assembled container with the tubing up to the filter 8 can be disposable. The only non-disposable part of the assembly is the pump 9 with its power switch and battery (not shown). The filter 8 can be reused until it is clogged. The choice of the disposable components ensures that no cross contamination of samples can result with this configuration. Contrary to the devices described in the prior art in which the volume of the sample is limited, in the disclosed device the pump can be operated for any amount of time in order to collect the microorganisms from either low or high volume samples.

Once the vacuum pump 9 is operated, a sample of ambient air is drawn by the collection tube 5 and transferred through the liquid media 3 where it is released in the form of air bubbles. Microorganisms in the air sample are interfaced to the liquid and subsequently mixed with the nutrient media. The sample is then conveyed through the linking tube 7 to the filter 8 where all particulate matter is prevented from reaching the vacuum pump 9.

The container is now ready for incubation. It can be placed in an incubator, which is set to a predetermined temperature for optimal growth. If live organisms are present in the media, they rapidly multiply following a "binary fission" process occurring during the generation time of the organism. If an indicator substance is also included in the media, it will transform once the organisms' concentration reaches a threshold level. This transformation occurs at time DT which is inversely proportional to the original concentration of organisms in the media, as described in U.S. Pat. No. 5,366,873:

$$\text{Log}(CFU/\text{ml}) = A - B*DT$$

Wherein DT is the Detection Time and A and B are constants depending upon the organism/media/temperature combination.

One of the obvious advantages of this approach is that the rapidity of the process depends upon the initial bacterial concentration in the media, while traditional colony growing techniques are slower and do not depend on the contamination level. In the device, the microorganisms accumulate in the liquid media. In other words, the bacterial concentration prior to the incubation phase depends upon the sampling time. Moreover, the longer the sampling time, the better the uniformity of the sample, the sample not being subject to statistical sampling errors.

Following the incubation phase, a small portion of the liquid media containing the target organisms can be removed from the container for further testing such as identification (taxonomy) tests, susceptibility to antimicrobial agents, DNA and PCR tests. The use of antimicrobial agents can also classify microorganisms that are resistant to certain agents. For example, incorporating weak anti-microbial agents that inhibit growth of regular environmental bacteria, but not resistive microorganisms (such as Anthrax), will indicate the presence of the pathogenic bacteria while eliminating false positive determinations of harmless organisms.

CONCLUSIONS, RAMIFICATIONS, AND SCOPE

Accordingly, it can be seen that a portable air sampler can be applied to obtain uniform environmental samples in accumulative fashion. Collecting the microorganisms in liquid media enables the process of microbial concentration and enables faster detection times. Using selective media, a pre-selected group of microorganisms may be cultured while other organisms are inhibited.

Although the description above contains many specificities, these should not be construed as limiting the scope of the invention but as merely providing illustrations of some of the presently preferred embodiments of this invention. Various other embodiments and ramifications are possible within it's scope. For example, multiple containers can simultaneously collect air samples, each containing a specific media/indicator combination in order to better classify the collected microorganisms. Or the method can be performed on a continuous air sampling basis instead of a batch (single sample) basis.

Thus the scope of the invention should be determined by the appended claims and their legal equivalents, rather than by the examples given.

What is claimed is:

1. A method for collecting and detecting suspect airborne microorganisms, comprising the steps of:

conveying a sample of suspect air into a culturing container containing liquid media that is capable of growing the suspect microorganisms and releasing the sample in said liquid media thereby forming air bubbles and intimately mixing and contacting the microorganisms with said liquid media;

incubating said culturing container at a pre-selected temperature chosen to promote fast multiplication of the microorganisms; and detecting chemical changes in said liquid media resulting from said multiplication thereby indicating the presence of the microorganisms.

2. The method of claim 1 wherein said liquid media is selective, promoting growth of a specific class of microorganisms while inhibiting growth of other microorganisms.

3. The method of claim 1 wherein said culturing container further contains indicator substance capable of detecting said chemical changes in said liquid media.

4. The method of claim 3 wherein said indicator substance is a dye capable of changing its color due to the presence of the microorganisms.

5. The method of claim 3 wherein said indicator substance is composed of fluorescing material capable of changing its fluorescence level due to the presence of the microorganisms.

6. The method of claim 3 wherein said indicator substance is a pH sensitive indicator.

7. The method of claim 3 wherein said indicator substance is an oxidation-reduction sensitive indicator.

8. The method of claim 3 wherein said indicator substance is an enzymatic sensitive indicator.

9. The method of claim 1 wherein said chemical changes are detected by an instrument comprising at least one sensor capable of sensing said chemical changes.

10. The method of claim 9 wherein said sensor is an optical sensor.

11. The method of claim 9 wherein said sensor is an electrical sensor measuring electrical properties of said liquid media.

12. The method of claim 9 wherein said sensor is capable of measuring carbon dioxide released by the microorganisms.

13. The method of claim 12 wherein said sensor is a pressure sensor measuring the pressure developed by said carbon dioxide released by the microorganisms.

14. The method of claim 1 further comprising transferring a liquid sample from said culturing container subsequent to said incubating, for additional testing of the microorganisms.

15. The method of claim 14 wherein said additional testing is PCR.

16. The method of claim 14 wherein said additional testing is DNA identification.

17. The method of claim 14 wherein said additional testing comprising growth of bacterial colonies on a nutrient substrate.

18. The method of claim 17 wherein said substrate is made of gelatin material.

19. The method of claim 18 wherein said gelatin material is agar.

20. The method of claim 14 wherein said additional testing is microbial taxonomy identification.

21. The method of claim 14 wherein said additional testing is anti microbial susceptibility testing.

* * * * *